(12) United States Patent
Hirashiki et al.

(10) Patent No.: US 10,568,806 B2
(45) Date of Patent: Feb. 25, 2020

(54) WEARABLE SITUATIONAL STRESS MANAGEMENT DEVICE

(71) Applicant: MINDFRAMERS, INC., San Ramon, CA (US)

(72) Inventors: Allen Hirashiki, San Ramon, CA (US); Carl J. Bailey, San Jose, CA (US); John Levy, Grass Valley, CA (US)

(73) Assignee: Mindframers, Inc., San Ramon, CA (US)

( * ) Notice: Subject to any disclaimer, the term of this patent is extended or adjusted under 35 U.S.C. 154(b) by 98 days.

(21) Appl. No.: 15/792,287

(22) Filed: Oct. 24, 2017

(65) Prior Publication Data

US 2018/0116906 A1 May 3, 2018

Related U.S. Application Data

(60) Provisional application No. 62/414,407, filed on Oct. 28, 2016.

(51) Int. Cl.
*A61N 1/36* (2006.01)
*A61H 39/00* (2006.01)
*A61N 1/04* (2006.01)

(52) U.S. Cl.
CPC ......... *A61H 39/002* (2013.01); *A61N 1/0476* (2013.01); *A61N 1/0484* (2013.01); *A61N 1/3603* (2017.08); *A61H 2201/5002* (2013.01); *A61H 2201/5007* (2013.01); *A61H 2201/5035* (2013.01); *A61H 2201/5048* (2013.01); *A61H 2201/5097* (2013.01); *A61H 2230/655* (2013.01)

(58) Field of Classification Search
CPC .... A61H 2201/5002; A61H 2201/5007; A61H 2201/5035; A61H 2201/5048; A61H 2201/5097; A61H 2230/655; A61H 39/002; A61N 1/0476; A61N 1/0484; A61N 1/3603
See application file for complete search history.

(56) References Cited

U.S. PATENT DOCUMENTS

| | | | |
|---|---|---|---|
| 4,981,146 | A | 1/1991 | Bertolucci |
| 5,944,514 | A | 8/1999 | Pohl |
| 6,012,926 | A | 1/2000 | Hodges |
| 6,178,352 | B1 | 1/2001 | Gruzdowich |
| 6,263,237 | B1 | 7/2001 | Rise |
| 6,735,480 | B2 | 5/2004 | Giuntoli |

(Continued)

*Primary Examiner* — George Manuel
(74) *Attorney, Agent, or Firm* — Antero Tormey & Petrin; Pete Tormey

(57) ABSTRACT

An electrical discharge device including an array of spring-load electrical contacts, said contacts electrically coupled to a multiplexer and a programmable power supply; a processor, said processor coupled to the power supply and the multiplexer; a memory, coupled to said processor, said memory including non-transitory, processor instructions operable to direct the processor to perform a method including measuring relative resistance between each pair of said electrical contacts, and applying a pre-determined electrical discharge to a pair of the electrical contacts in response to said measuring. Embodiment includes applying at least a portion of the electrical contacts to human skin substantially near an acupoint wherein said pair of electrical contacts is the pair having the least resistance between them.

12 Claims, 8 Drawing Sheets

(56) References Cited

U.S. PATENT DOCUMENTS

| | | | |
|---|---|---|---|
| 9,592,393 B2* | 3/2017 | Stahmann | A61N 1/3708 |
| 2003/0195583 A1 | 10/2003 | Gruzdowich | |
| 2004/0167588 A1 | 8/2004 | Bertolucci | |
| 2012/0323149 A1 | 12/2012 | Chou | |
| 2015/0213724 A1 | 7/2015 | Shoshani | |
| 2015/0360030 A1* | 12/2015 | Cartledge | A61N 1/36036 607/60 |

* cited by examiner

WEARABLE SITUATIONAL STRESS MANAGEMENT DEVICE

PRIORITY

This application claims the benefit of provisional application 62/414,407 filed Oct. 28, 2016, by the same inventors, which is included by reference as if fully set forth herein.

BACKGROUND

Acustimulation, the continuous application of mild electrical discharges on the skin at acupoints, may provide the benefits of acupuncture in out-of-clinic settings. Devices using acustimulation, such as the RELIEFBAND (FDA approved for nausea), are primitive in the application of electrical discharges, and may cause discomfort and involuntary muscle contractions.

The application of advanced nerve stimulation technology on acupoints may increase effectiveness and user acceptance. For example, and without limitations, the acupuncture point H7 is one acupoint where acustimulation with advanced technology may block the symptoms of anxiety.

Acupuncture points are frequently described as having distinct electrical properties. These properties include increased conductance, reduced impedance and resistance, increased capacitance, and elevated electrical potential compared to adjacent non-acupuncture points.

Accordingly, there is a need to better devices and techniques for the application of Acustimulation.

SUMMARY

Figure 1:
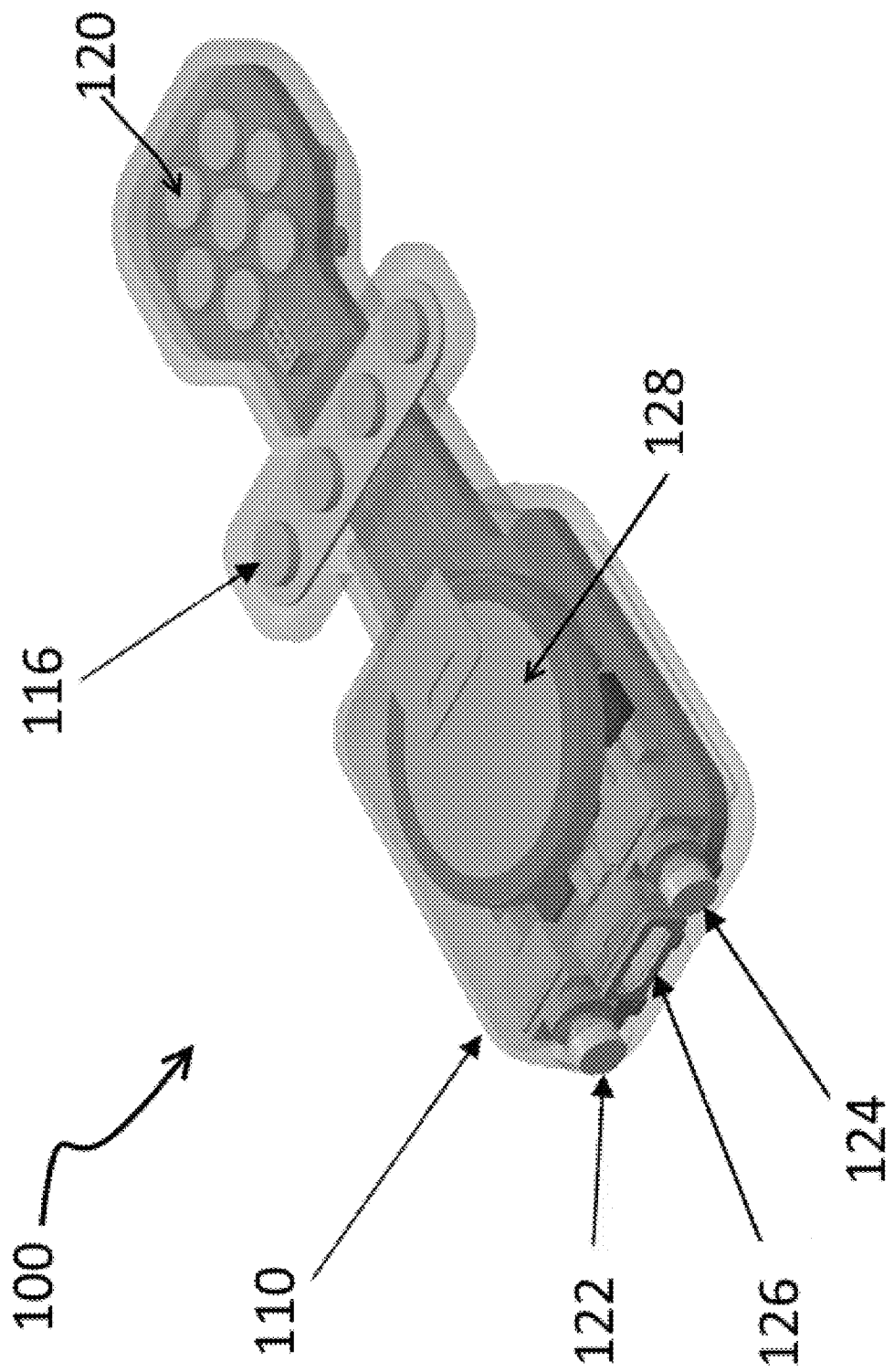
FIG. 1 shows a top view of an embodiment of a wearable situational stress management device.

Disclosed herein is an electrical discharge device including an array of spring-load electrical contacts, said contacts electrically coupled to a multiplexer and a programmable power supply; a processor, said processor coupled to the power supply and the multiplexer; a memory, coupled to said processor, said memory including non-transitory, processor instructions operable to direct the processor to perform a method including measuring relative resistance between each pair of said electrical contacts, and applying a pre-determined electrical discharge to a pair of the electrical contacts in response to said measuring. Embodiment includes applying at least a portion of the electrical contacts to human skin substantially near an acupoint wherein said pair of electrical contacts is the pair having the least resistance between them.

Generality of Invention

This application should be read in the most general possible form. This includes, without limitation, the following:

References to specific techniques include alternative and more general techniques, especially when discussing aspects of the invention, or how the invention might be made or used.

References to "preferred" techniques generally mean that the inventor contemplates using those techniques, and thinks they are best for the intended application. This does not exclude other techniques for the invention, and does not mean that those techniques are necessarily essential or would be preferred in all circumstances.

References to contemplated causes and effects for some implementations do not preclude other causes or effects that might occur in other implementations.

References to reasons for using particular techniques do not preclude other reasons or techniques, even if completely contrary, where circumstances would indicate that the stated reasons or techniques are not as applicable.

Furthermore, the invention is in no way limited to the specifics of any particular embodiments and examples disclosed herein. Many other variations are possible which remain within the content, scope and spirit of the invention, and these variations would become clear to those skilled in the art after perusal of this application.

Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Read this application with the following terms and phrases in their most general form. The general meaning of each of these terms or phrases is illustrative, not in any way limiting.

Lexicography

The term "Acupoint" generally refers to locations on a body that are the focus of acupuncture, acupressure, sonopuncture and laser acupuncture treatment.

The term "Acustimulation" generally refers to mild stimulation, often by transcutaneous, electrical stimulation of acupuncture points done for therapy.

The term "Adaptation" generally refers to a point when a body becomes accustomed to stimulus or drugs.

The phrase "Situational stress" generally refers to the stress someone puts on themselves such as giving a speech or taking a test.

DETAILED DESCRIPTION

FIG. 1 shows a top view of an embodiment of a wearable situational stress management device 100. In FIG. 1 is a waterproof, hypo-allergenic class 5 medical grade silicone rubber case 110 which operates to avoid cytotoxicity, genotoxicity, delayed type hypersensitivity and irritation when in contact with a user's skin. One having skill in the art will appreciate that other materials may be employed to provide similar advantages and that this disclosure should not be limited in any way.

Also shown in FIG. 1 are spring-loaded, metallic-plated contacts 120 aligned in a hexagonal-shaped contact array. The metallic plating may be made with gold or other suitable electrical conductive material. A switch 122, is coupled to control electronics for turning the device on and off, and a second switch 124 is coupled to control circuitry to provide for calibration (described below). A micro USB port 126 is coupled to control electronics to provide for charging an internal battery 128 and to function as a communications port to allow for communications with the control circuitry. An array of magnets 116 is shown for removably coupling the device 100 to a wrist band which may be formed with a complementary array of magnets (not shown). This allows for positioning of the device 100 and securely holding it in place, which in certain embodiments, may include holding it in place using a smartphone, fitness tracker, and the like.

Figure 2:
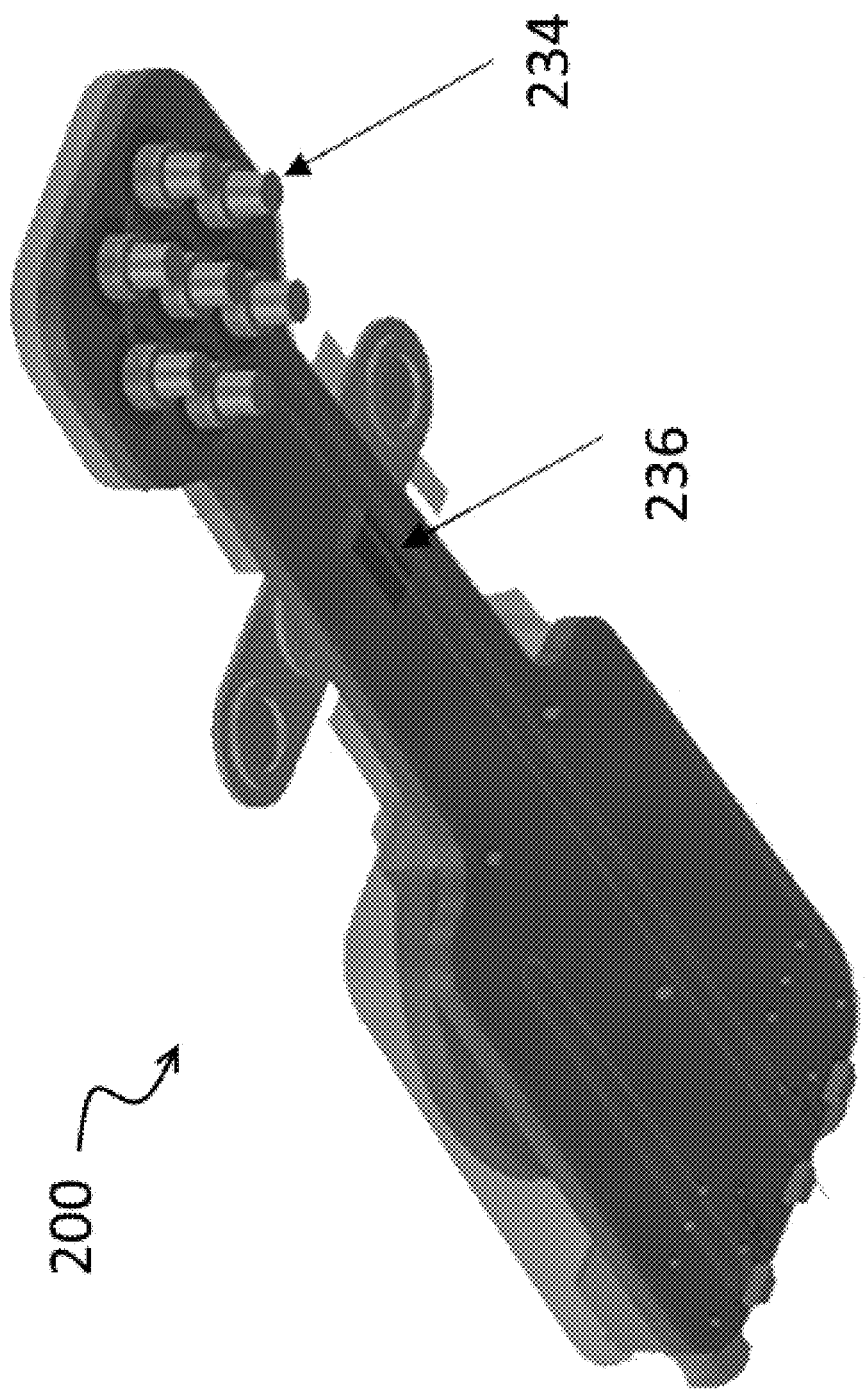
FIG. 2 shows a bottom view (or skin side) of an embodiment of a wearable situational stress management device.

FIG. 2 shows a bottom view (or skin side) of an embodiment of a wearable situational stress management device 200. In FIG. 2 the metallic-plated spring-loaded contacts 234 are aligned in a hexagonal-shaped contact array and are shown extending outwards from the device 200. The metallic plating may be gold, or in certain embodiments, any electrically conducting material such as elastomers, copper or other suitable material may be used. Moreover, solid material and not plating may be employed.

In operation, the contact array is placed across the skin with enough pressure to partially compress the springs within each contact. A full compression stroke of a contact pin is not required, because a minimum compression may provide the intended pressure and electrical conductivity. Once the array is in place, control circuitry (described below), may accurately and automatically detect the targeted acupoint when placed in the general vicinity of the acupoint. Sensors 236, such as heart rate/heart rate variation and arterial oxygen saturation (SpO2) sensors, may be attached to a surface of the device 200 such that the sensors have visible access with the skin when the device 200 is worn. This provides for heart rate, oxygen content in the blood and other information to be measured by control electronics.

Figure 3:
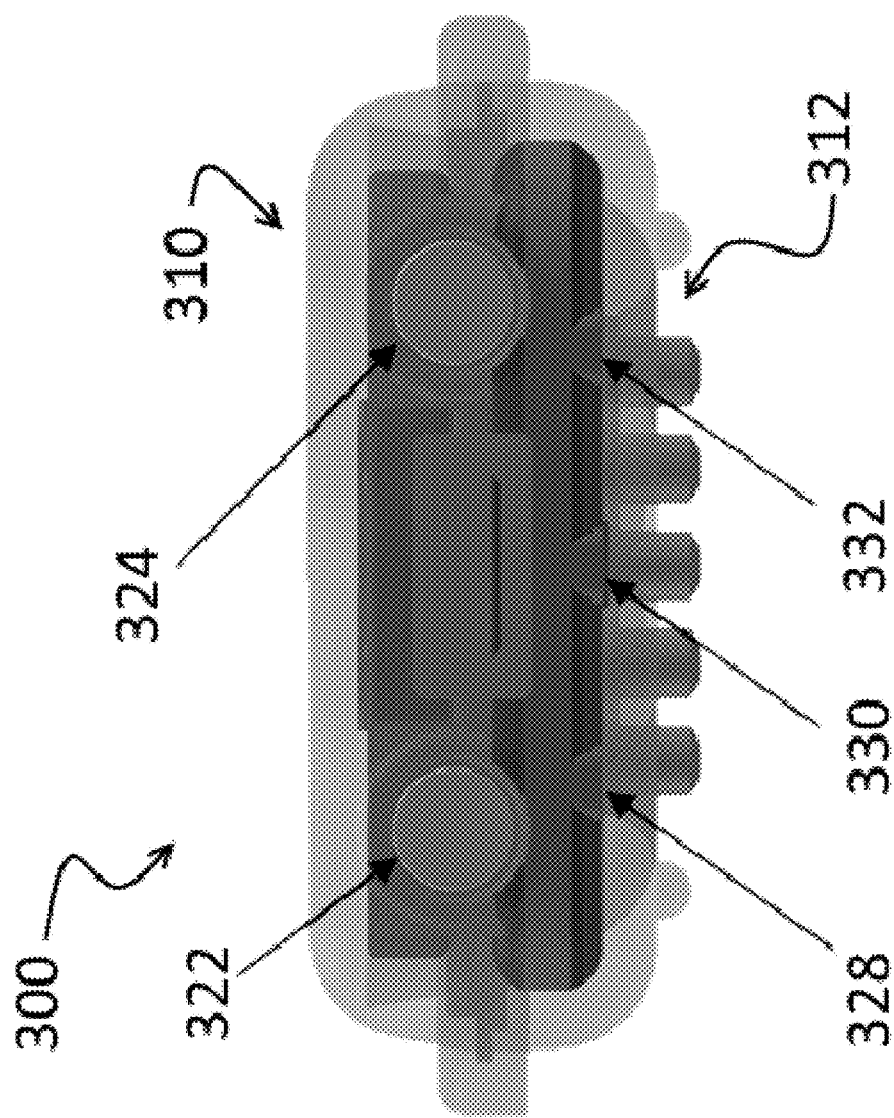
FIG. 3 shows a proximal end view of an embodiment of a wearable situational stress management device.

FIG. 3 shows a proximal end view of an embodiment of a wearable situational stress management device 300. In FIG. 3 a top side 310 is mated to a bottom side 312, which may be a single overmold of silicone rubber. FIG. 3 shows an on/off switch 322, and a calibration switch 324. In addition to the switches described, FIG. 3 shows a series of light emitting diode (LED) indicators 328, 330, and 332 electrically coupled to the control circuitry. The LEDs may be multi-definition tri-color (RGB) indicators to provide user feedback during sleep, operational, upgrade and charging modes or other indications to a user.

References in the specification to "one embodiment", "an embodiment", "an example embodiment", etc., indicate that the embodiment described may include a particular feature, structure or characteristic, but every embodiment may not necessarily include the particular feature, structure or characteristic. Moreover, such phrases are not necessarily referring to the same embodiment. Further, when a particular feature, structure or characteristic is described in connection with an embodiment, it is submitted that it is within the knowledge of one of ordinary skill in the art to effect such feature, structure or characteristic in connection with other embodiments whether or not explicitly described. Parts of the description are presented using terminology commonly employed by those of ordinary skill in the art to convey the substance of their work to others of ordinary skill in the art.

System Elements

Figure 4:
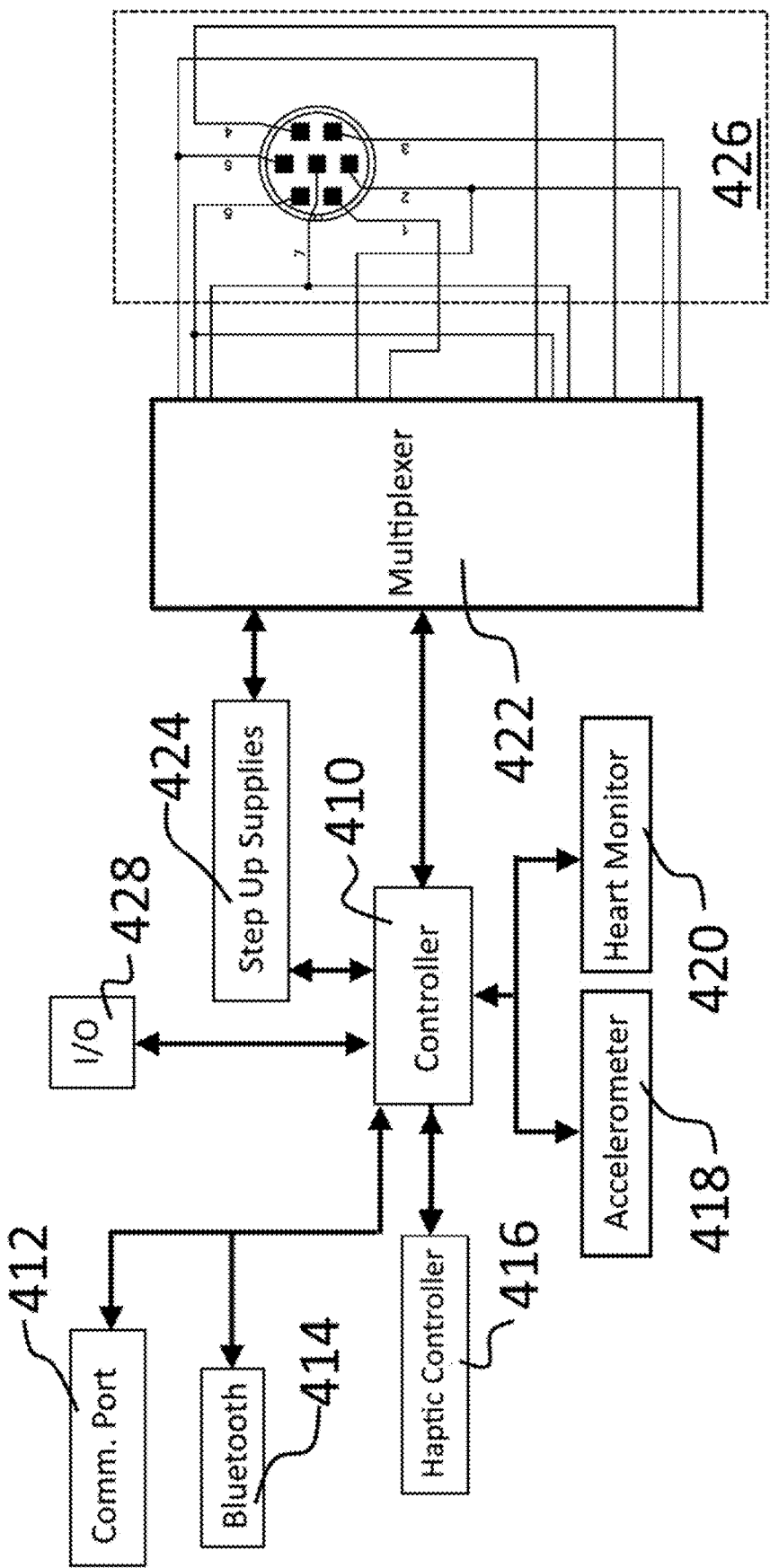
FIG. 4 shows a block diagram of certain elements of the current disclosure.

FIG. 4 shows a block diagram of certain elements of the current disclosure. In FIG. 4 a controller 410 is coupled to various system elements. These elements include, but are not limited to communications ports 412, Bluetooth 414, which may be Bluetooth low energy (BLE) or other wireless circuits, haptic driver 416, an accelerometer 418, a heart monitor 420, various input output (TO) devices 428 such as light emitting diodes (LEDs) and switches, and multiplexers 422. The multiplexers are further coupled to step up supplies 424 and to an array of electrical contacts 426.

Certain embodiments may be effectuated using a MAX32600 microcontroller by Maxim Integrated Products, although other small-sized integrated controllers may also be employed to effectuate the same or similar results. The controller may use an industry-standard ARM® Cortex®-M3 32-bit RISC CPU together with 256 KB of flash memory, 32 KB of SRAM, a 2 KB instruction cache, and integrated high-performance analog peripherals for operating sensors, LEDs and other input output (I/O) functions.

Bluetooth low energy (BLE) and 2.4 GHz operations may be effectuated using convention devices such as CC2541 from Texas Instruments. The haptic controller 416 may include one or more of a DRV2667 by Texas Instruments to amplify low level waveforms to high voltage.

The step up supplies 424 may be effectuated using conventional devices such as the LT 1615/LT1615-1 step-up DC/DC converters by Linear Technologies. The step-up supplies 424 may provide for 350 mA current limit and an input voltage range of 1.2V to 15V. The supply 424 allows high voltage outputs up to 34V to be generated with boost topology without requiring transformers.

The multiplexers 422 may be effectuated by conventional devices such as Maxim Integrated Technologies MAX14752/MAX14753 high-voltage analog multiplexers. The multiplexers operate to provide both positive and negative polarity voltages to the array of electrical contacts 426 under control of the controller 410. The shape of the array of electrical contacts 426 is determined by operation considerations described below. While shown as seven contacts arranged in a particular array, this disclosure should not be limiting in any way because the inventors contemplate using different shaped arrays of contacts for operations on differing acupoints.

Indicators

Some embodiments may include light emitting diodes (LEDs) to indicate certain operations. These indicators may work with a switch to indication feedback or other processes. For example, and without limitation:
Power on;
Activate intensity setting/calibration;
Increase/reduce intensity;
Bluetooth pairing;
Connection to mobile application;
Power off.

Operations

The system elements are coupled to a microcontroller 410 which includes memory for holding processor instructions. The operations described herein may be effectuated using the system elements under control of the microcontroller. In certain embodiments this disclosure describes applying electrical impulses at predetermined acupoints. For example, and without limitation, stimulation of acupoint H7 may block situational stress. Accordingly features may include a miniature, waterproof, self-contained, battery powered device encased in hypo-allergenic class 5 medical grade material such as silicone rubber. A highly stretchable medical grade silicone rubber retention wrist strap may be embedded with magnets to magnetically couple to mating magnet on the device, thereby eliminating the need for buckles to hold and position the device securely on a user and for providing concealment as disclosed herein.

Calibration

A user may trigger calibration mode by pressing the on/off button repeatedly to advance through a number of pre-determined settings stored in memory. In some embodiments the calibration button may be effectuated using the on/off button. Calibration may be complete when the user can feel the discharge as a tingling sensation at the acupoint region or distal in the hand and may lower intensity setting by pressing second button once.

Acupoint Positioning

Embodiments disclosed herein may provide for automatic location detection of acupoints. The location detection may include the use of galvanic skin response (GSR) using spring loaded sliding contacts. The smaller the contact and spacing, the more accurate acupoint selection may be. In addition, the spring-loaded pressure reduces resistance at the skin surface allowing for the use of lower electrical intensity and more reliable measurement. Moreover, the equally spaced array of spring-loaded contacts permits many possible electrical discharge gaps and maximum geometric coverage within contact array boundary.

By alternating the polarity of contacts in the array, the geometric pattern allows discharge between every pair of contacts. For example, and without limitation, in the hex formation with center pattern, fixed polarity values may have up to nine discharge pairs, but by alternating polarity of contacts, twelve discharge are possible with same number of contacts. Using the discharge pairs allows for automatically finding the lowest resistance between two points on the skin. Since acupoints have been measured to have a lower electrical resistance, the array of contacts provides multiple adjacent areas to find which pair of contacts measure the lowest resistance. This pair becomes the contact pair for electrical discharge to the skin.

Over the course of wearing the device, physical parameters may change. For example, the position may shift due to user movement or perspiration levels may change from environmental or other factors. If galvanic skin response (GSR) measurements are taken before each discharge, the array will detect the change in resistance across all positions and maintain constant discharge intensity as well as auto redirect to the lowest resistance point, thus effecting a self-compensating and self-correcting operation.

Some embodiments may provide for autonomous determination of session operation duration and intensity based on biometric data from sensors. For example, and without limitation, if the process blocks a user's stress enough to affect a response such as a lowering of heart rate and less sweating, historical use data will compare operating duration and use that to determine lowering of intensity as well as when to shut off discharges and enter into a sleep mode. This effects automatic operation for minimizing time and intensity of nerve exposure to acustimulation. This may operate to prevent or delay onset of any adaptation phenomenon which may occur.

Embodiments using flat contacts conventionally work better with a film of conductive gel on the skin surface. However, gel is a deterrent for regular use of any device with flat contacts. Using a device with flat contacts without gel requires a higher discharge intensity to overcome the skin's surface resistance. The spring-loaded pin contact array does not need conductive gel to provide a low resistance path on the skin surface because the localized normal force applies a greater pressure than possible with a larger flat contact. Also, the localized soft spring force of the pins is more comfortable to the user.

Acustimulation

In operation, an excitation waveform may be generated in low level digital circuits and stored in memory. The low level waveform is amplified to a voltage with an amplitude between 10V and 50V peak to peak. Associated circuitry as disclosed herein, generates a train of voltage pulses with variable amplitude with a sine wave envelope in some embodiments. The voltage waveform may repeat at a fixed rate, such as every 4 seconds. The voltage train generated may be made up of positive and negative pulses. Pulse width may be in the approximately 50 to 60 micro seconds range and about 30 milliseconds apart. In one exemplary embodiment, the excitation voltage pulse amplitude may be varied by the value of a sine wave with a half period of 4 seconds. With 0.03 second spacing between pulses, a total of 132 pulses are generated. The peak sine wave voltage level is 1 Volt at 2 seconds and decreases to zero voltage at 4 seconds. The envelope voltage level can be varied by using a multiplier between 0 and 2 V peak to peak, and after voltage amplification, voltages up to 50V peak to peak may be generated.

In other embodiments, alternate waveform generation may be used to effect results. For example, and without limitation, the discharge circuit may have ten waveforms, each with a different amplitude, shape, and frequency stored in CPU memory that provide the ten various settings.

The current may be up to 1 mA and monitored by the controller. Measuring galvanic skin response (GSR) allows for determining the post-calibrated and ongoing discharge level delivered through the contacts. GSR factors used by this disclosure may include:

Resistance changes across contacts based on contact-to-skin pressure

Salt concentration level in perspiration

Position of contacts relative to the acupoint H7 on the inner wrist

This enables the discharge control circuit to maintain a constant output despite changes that could cause a spike in perceived discharge intensity, resulting in being startled or feeling discomfort from intensity levels higher than the user's calibration level. When GSR circuit detects no contact or resistance within skin values of 25 k ohms+/−10 k ohms, discharge is quickly stopped. This prevents unplanned discharge if removed from user while operating or attempts made to operate without being applied to skin. In some operations the process waits for up to 10 seconds before checking GSR again. If skin resistance is measured, operational mode resumes. If after ten consecutive checks with no skin resistance measured, the process may enter a sleep mode. In some preferred embodiments each activation and calibration provides 15 minutes of acustimulation before automatically shutting off discharges and going into sleep mode.

Cyclic Operations

In some embodiments operational mode is set to a pre-determine amount of cycles, for example and without limitation, 225 cycles at four seconds per cycle (fifteen minutes). Each cycle starts by measuring GSR across all twelve possible combinations of contacts in the array to determine the desired acupoint, and stores it in CPU memory. The cycle ends when the correct contact pair receives the discharge waveform. While device is in operational mode, voltage is applied across two of the pre-selected contacts at a frequency and waveform to penetrate the skin without causing muscle contractions or tingling.

Sensors, such as heart rate/heart rate variation and SpO2 may contribute toward autonomous operation by comparing changes in user biometric data to determine if the default period was effective or if additional discharge time is required.

In other embodiments the default duration may be adjusted in response to the minutes of acustimulation based on the biometric data gathered during previous activations or by a user setting using an associated device (i.e. smartphone, tablet) application. The device application may be paired initially and automatically associated with a unique serial number set in CPU memory during manufacturing.

Sleep Operation

In operation, sleep may be enhanced because certain embodiments employ historic data recording to build an algorithm to track sleeping patterns. In these embodiments a sleep tracking feature of an associated application on a separate smart device may measure movement with the accelerometers. When combined with a smart device such as a smart phone, the process may leverage the computing power in smartphones and other devices to automatically turn on discharge cycles prior to waking or turn off when sleeping, based on movement detected by the accelerometer. Moreover, combining changes in heart rate with motion will better gauge the waking state of the user. Some embodiments may employ an algorithm to compare dream state elevation to sleep state and turn on discharging to reduce fitful sleep or to prevent or lessen awakening prior to desired wake up time.

Certain embodiments may also provide for operations for users suffering sleep apnea by monitoring blood oxygen saturation (SpO2) conditions where acustimulation may provide a benefit. In these embodiments a smart device might also indicate the alarm condition. Moreover, historical variations in SpO2 may provide trend analysis for tracking the condition.

Multi Point Stimulation

Some embodiments may use the communications port or Bluetooth to synchronize operations with another similar device. In this embodiment two devices would be coupled to an application running on a smartphone or another device. By operating in tandem, simultaneous multi-acupoint applications may be mirrored on a user's body meridians. By treating multiple known acupoints for blocking stress or other disorders, the efficiency of the treatment may improve. Yet controlling multiple linked devices may be difficult unless a remote device (smartphone or tablet) provides a master/slave relationship between multiple devices. For example, and without limitation, a master device, operating through an associated application, can compare sensor data (heart rate, GSR and motion detection), in addition to reporting the common slave functions of discharge and battery status via wireless protocols such as Bluetooth.

To effectuate multi-point stimulation, the associate application may map locations of all devices, acupoints, and control settings from user settings or automatically from their respective algorithm to achieve a higher degree of effectiveness.

In these embodiments, the ability to synchronize or shift discharge phases may help defer adaptation and desensitization problems with a wearable device. The ability to moderate discharge intensity based on feedback from sensors providing heart rate, GSR and motion data using algorithms in the smartphone or tablet application may allow for discharge levels below a user's tingle perception. Tingling is debilitating and disruptive to concentration, so operation below this level is beneficial. The ability to turn off discharges and enter dormant sleep mode yet reactivate as sensors detect activation levels avoids unnecessary nerve stimulation, deferring adaptation and over stimulation.

Since nerve networks are mirrored in the limbs, better results may be achieved when simultaneous application occurs on mirrored acupoint locations such as arms and legs—thus two devices may be paired to operate in tandem to achieve better results.

Associated Application

In some embodiments a mobile application, running on a remote device may be coupled through Bluetooth or a communications port to provide more functionality. This functionality may include programmable waveforms and synchronization of operation parameters.

Figure 5:
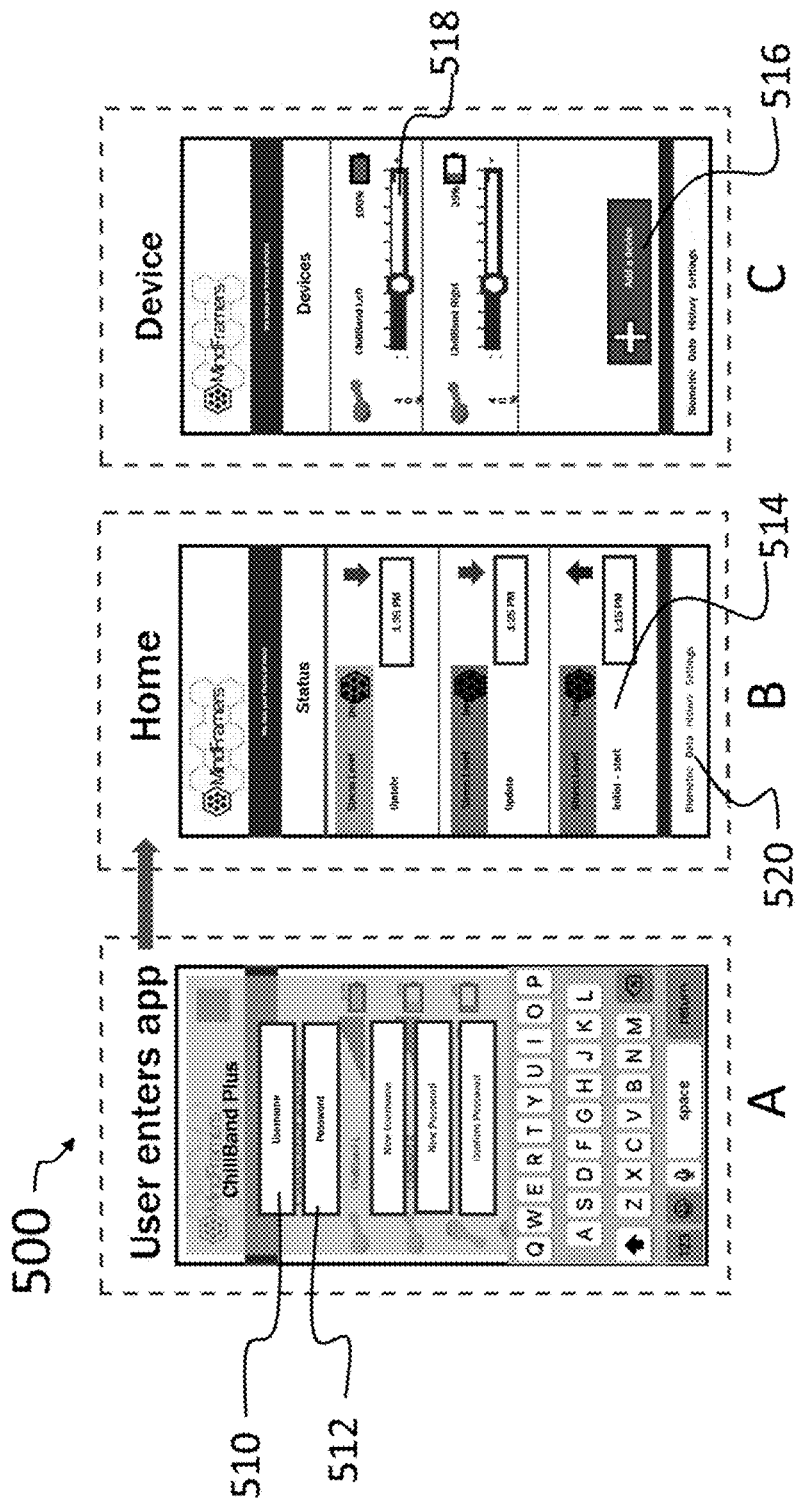
FIG. 5 shows an embodiment of a mobile application for operations on smart devices such as smartphones and tablets.

FIG. 5 shows an embodiment of a mobile application for operations on smart devices such as smartphones and tablets. In FIG. 5 the application is coupled to a device that includes at least some of the elements described herein. In FIG. 5A security is effectuated using a username 510 and password 512 combination. After authentication, control passes to a FIG. 5B where a user's recent stress history 514 is displayed showing trends and controls 520 for more operations. In FIG. 5C multiple devices 518 (each labeled as "Chillband") are displayed showing their battery power indication and providing an opportunity to add additional devices with control 516. Controls 520 pass operation off to other screens such as FIG. 6.

Figure 6:
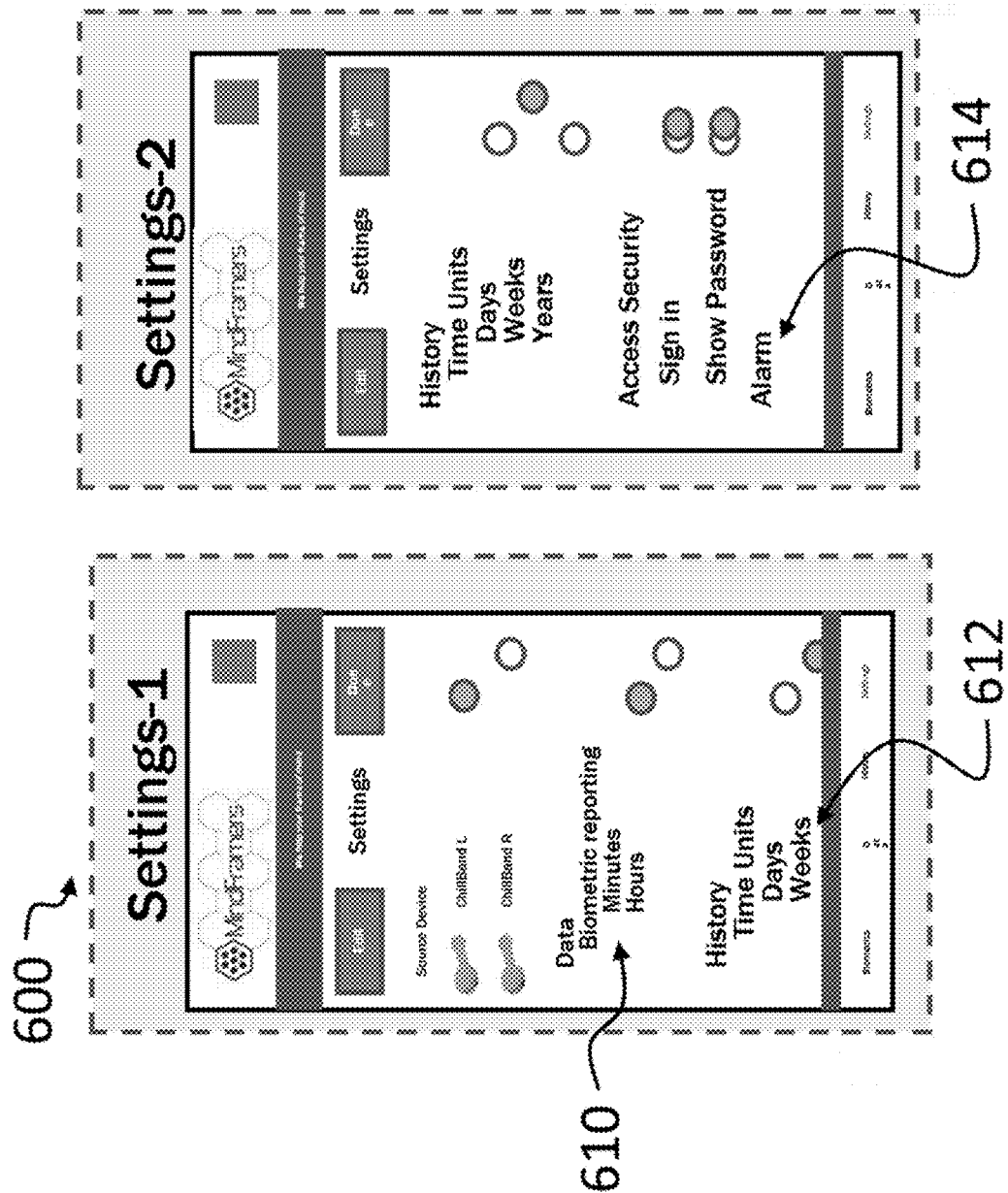
FIG. 6 shows embodiments of application software for controlling the biometric process settings and others.

FIG. 6 shows embodiments of application software for controlling the biometric process settings 610, history information 612, and other settings such as alarms 614.

Figure 7:
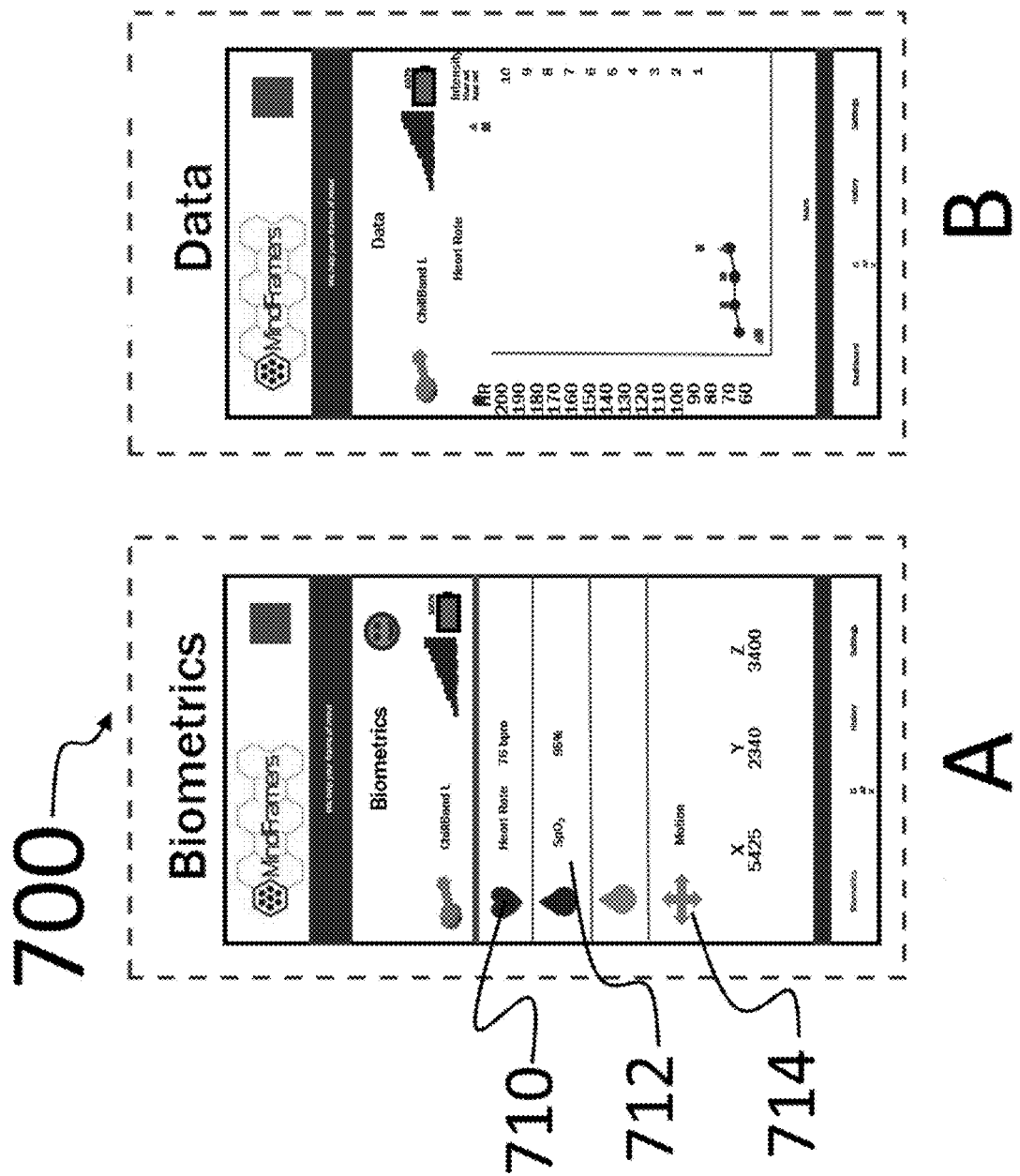
FIG. 7 shows several views of application software in conformance with the present disclosure.

FIG. 7 shows several views of application software in conformance with the present disclosure. In FIG. 7A biometric information from sensors such as heart rate 710, arterial oxygen saturation (SpO2) 712, and accelerometer (motion) information 714 is displayed. In FIG. 7B representative correlation information (heart rate and discharge intensity) is displayed.

Concealment

Figure 8:
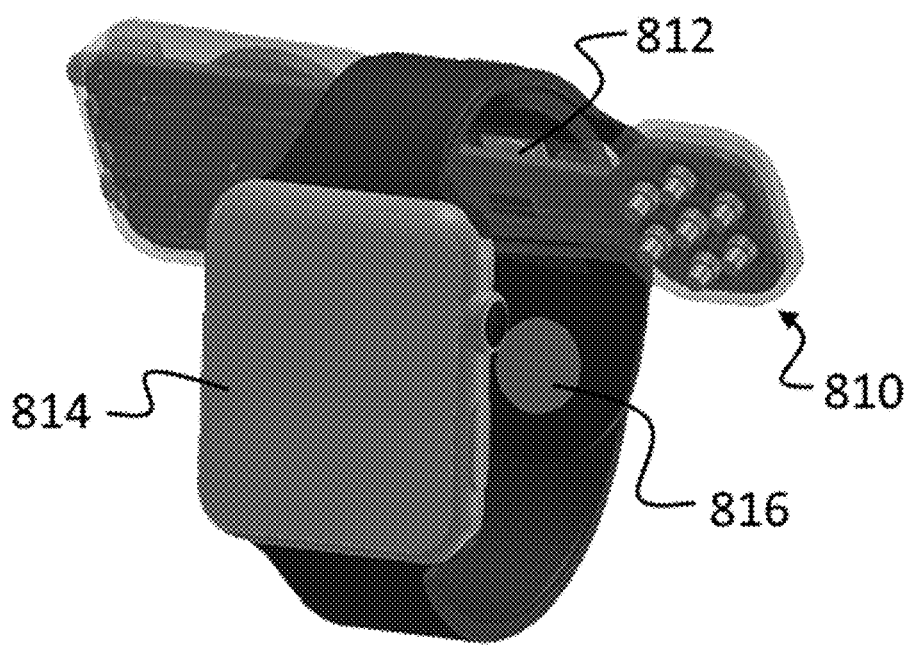
FIG. 8 shows an industrial design of one embodiment of an acustimulation device.

FIG. 8 shows an industrial design of one embodiment of an acustimulation device. This embodiment accommodates a user desire to conceal the fact they are using it, similar to the desire to conceal hearing aids. Placing a contact array 810 at a distal end and control electronics at a proximal end enables concealed wear. In the middle of the device, a magnetic wrist strap positions itself perpendicular to the device by mating with magnets 812 in the device and on the strap 816. Further concealment and convenience can be obtained by attaching the device to a wrist using a fitness tracker or wristwatch 814.

Maximum concealment may be provided by a stretchable fabric tube wrap to snugly cover the device (not shown). This is optimized for wear under long sleeves and can be provided in colors to match fabrics or flesh tones. Fabric is breathable and stretches to accommodate full or partial coverage of the device. Concealment by disguise can be attained by deliberately using patterns and/or bright colors to cover the device as a fashion accessory and not bring attention by mismatching fabric and skin tones.

APPENDIX

Additional embodiments of the current disclosure may be effectuated using information described in the attached appendix. Accordingly, the appendix is incorporated by reference as if fully set forth herein.

The above illustration provides many different embodiments or embodiments for implementing different features of the invention. Specific embodiments of components and processes are described to help clarify the invention. These are, of course, merely embodiments and are not intended to limit the invention from that described in the claims.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

We claim:

1. An electrical discharge device including:
an array of spring-loaded electrical contacts, said contacts electrically coupled to a multiplexer and a programmable power supply;
a processor, said processor coupled to the power supply and the multiplexer;
a memory, coupled to said processor, said memory including non-transitory, processor instructions operable to direct the processor to perform a method including:
measuring relative resistance between each pair of said electrical contacts,
identifying which pair of electrical contacts has the least resistance between them, and applying an electrical discharge to the pair of the electrical contacts in response to said identifying,
wherein said electrical discharge includes a voltage of between ten and fifty volts.

2. The device of claim 1 further including:
a wireless communications port, coupled to said processor, wherein the method further includes communicating, through the wireless communications port, electrical discharge information.

3. An electrical discharge device including:
an array of spring-load electrical contacts, said contacts electrically coupled to a multiplexer and a programmable power supply;
a processor, said processor coupled to the power supply and the multiplexer;
a memory, coupled to said processor, said memory including non-transitory, processor instructions operable to direct the processor to perform a method including:
measuring relative resistance between each pair of said electrical contacts, and applying a pre-determined electrical discharge to a pair of the electrical contacts in response to said measuring.

4. The device of claim 3 wherein the method includes applying at least a portion of the electrical contacts to human skin.

5. The device of claim 4 wherein the human skin is substantially near an acupoint.

6. The device of claim 3 wherein said pair of electrical contacts is the pair having the least resistance between them.

7. The device of claim 3 further including:
A wireless communications port, wherein the method further includes communicating, through the wireless communications port, acustimulation information.

8. The device of claim 7 wherein the method further includes communicating, through the wireless port, biometric information.

9. The device of claim 7 wherein said communicating is with a remote processing device, said remote processing device including control software operable to transmit and receive acustimulation information.

10. The device of claim 7 wherein said communicating is with a remote device substantially similar to the device of claim 1.

11. The device of claim 3 wherein the predetermined discharge is a pulse of between ten and fifty volts.

12. The device of claim 3 wherein the predetermined discharge is one of either a sine wave, a pulse, or a ramp wave.

* * * * *